United States Patent [19]

Scott

[11] 4,062,939

[45] Dec. 13, 1977

[54] PERFLUOROCARBON RESINS IN A HAIR AND SCALP CONDITIONING AND CLEANSING COMPOSITION

[75] Inventor: Howard L. Scott, Philadelphia, Pa.

[73] Assignee: Widner College, Chester, Pa.

[21] Appl. No.: 620,330

[22] Filed: Dec. 15, 1975

Related U.S. Application Data

[63] Continuation-in-part of Ser. No. 430,912, Jan. 4, 1974, Pat. No. 3,911,106, which is a continuation-in-part of Ser. No. 358,897, May 10, 1973, abandoned, which is a continuation-in-part of Ser. No. 128,534, March 26, 1971, abandoned.

[51] Int. Cl.² ............................................. A61K 7/06
[52] U.S. Cl. ........................... 424/70; 252/DIG. 2; 252/DIG. 3; 252/DIG. 13; 252/545; 424/DIG. 2; 424/71; 424/78

[58] Field of Search ............... 424/70, 71, 78, DIG. 2; 260/29.6 F; 252/DIG. 2, DIG. 3, DIG. 13, 545

[56] References Cited

U.S. PATENT DOCUMENTS

| | | | |
|---|---|---|---|
| 2,613,193 | 10/1952 | Osdal | 260/29.6 F |
| 3,133,865 | 5/1964 | Richardson et al. | 424/71 |
| 3,301,807 | 1/1967 | Hoashi | 260/29.6 F |
| 3,707,519 | 12/1972 | Hahn | 260/29.6 F |
| 3,755,235 | 8/1973 | Sianesi et al. | 260/29.6 F |

*Primary Examiner*—Albert T. Meyers
*Assistant Examiner*—Vera C. Clarke
*Attorney, Agent, or Firm*—Arthur A. Jacobs

[57] ABSTRACT

A hair and scalp conditioning and cleansing composition which contains perfluorocarbon resins as lubricating and/or scouring agents is disclosed.

1 Claim, No Drawings

PERFLUOROCARBON RESINS IN A HAIR AND SCALP CONDITIONING AND CLEANSING COMPOSITION

This application is a continuation-in-part of co-pending application Ser. No. 430,912, filed Jan. 4, 1974, now U.S. Pat. 3,911,106, which is itself a continuation-in-part of application Ser. No. 358,897, filed May 10, 1973, now abandoned, which is also a continuation-in-part of application Ser. No. 128,534, filed March 26, 1971, now abandoned.

The present invention relates to the manufacture of cosmetic preparation for the hair and scalp employing as a lubricating agent perfluorocarbon resins. The invention further relates to a durable dry and inert scouring agent for shampoos, in liquid, gelled or solid form, that will not break down or get wet during use and that comprises a selection from the group of resinous perfluorocarbons.

The resins of chlorotrifluorethylene have also been found to be effectively useful in cosmetic and shampoos in conditioning and cleansing the hair and scalp.

Further, in accordance with the present invention, it has been found that the family of perfluorocarbon resins are effective conditioning and cleansing agents for the hair and scalp by rubbing thereinto or thereon an effective amount of these resins having a molecular weight of between about 1,000,000 and about 10,000,000 and a viscosity greater than $10^{10}$ poises at about 300° C. The amount used may vary widely depending on the type and condition of the hair and scalp, but may be easily determined by the user and his or her individual requirements.

Perfluorocarbon resins within the scope of this invention include the homopolymer of hexafluoropropylene, and the copolymer of tetrafluoroethylene and hexafluoropropylene having the formula $(-CF_2CF_2-CF_2CF\ CF_3)_n$. These resins have a specific gravity of about 2.18–2.24, and a melting point of over 600° F.

Subject resins may be used in aqueous composition or diluted in any feasible diluent (especially fatty alcohols such as hexadecyl alcohol, triethanolamine lauryl sulfate, or the like, or oils such as mineral oils, vegetable oils, or the like). It is also often desirable to include a thickening, dispersing and emulsifying agent as well as a dressing agent. Any well-known thickening, dispersing or emulsifying agent may be used, as for example, fatty alcohols such as those derived from coconut oil and the like, methyl cellulose, carboxy polymethylene, and any others which are well-known in the art. The dressing agent may be also any one or more of the many-well-known products generally used for this purpose. Among such products are lanolin, petrolatum, mineral oil, and the like. There may also be included a antibacterials agent and a base such as sodium hydroxide or the like if required to raise the pH of the composition to prevent undue acidity.

The thickening, dispersing and emulsifying agent may, as stated above, be any one of a number of products having such properties. Preferably used is a carboxypolymethylene having a molecular weight of about 2,500,000 and a specific gravity of about 1.41. Such product is a vinyl polymer having active carboxyl groups, which is highly ionic and slightly acidic. Such carboxypolymethylenes are produced by B. F. Goodrich Company under the name of "Carbopol" resins. This carboxypolymethylene component when used, is preferably in a proportion of about 0.2–5% by weight. Methyl cellulose is another thickening and emulsifying agent useful in this invention and sold under the trade name "Methocel".

The antibacterial agent may be any one of a number of compatible compounds having germicidal properties and which are compatible with the other ingredients. There are many quaternary ammonium compounds in this category. Among such compounds are benzalkanium chloride, dodecyl dimethyl benzyl ammonium saccharinate, and a large variety of other well-known and commercially available quaternary ammonium antibacterials. A particular compound which is preferably used is dehydroacetic acid. Sorbic acid is also highly useful. Any of these antibacterials, when used, are present in a preparation of about 0.1–3% by weight.

The following examples are illustrative of the present invention:

EXAMPLE NO. 1

A composition was prepared using 3% by weight of hexafluoropropylene resins, 1.0% by weight of "Carbopol", 15% by weight of petrolatum, 5% by weight of isopropanol, 1.0% by weight of the antibacterial agent, dehydroacetic acid, 1.0% by weight of diethanolamine, and water to make 100% by weight total.

The "Carbopol" was first mixed with the water with agitation. This was immediately followed by the addition of the petrolatum, the resin, the isopropanol, the antibacterial agent and the diethanolamine in succession, while rapid agitation is continued. The agitation was continued until the composition became too viscous to mix easily. It was then set aside for about 30 minutes. Then it was again agitated for several minutes until a smooth homogeneous gel was produced. The entire process was conducted at room temperature and pressure.

The product produced in the above manner was a smooth, white cream that is adapted to be rubbed into the hair and scalp.

EXAMPLE NO. 2.

| Shampoo, Liquid | % |
|---|---|
| Triethanolamine lauryl sulfate, 40% | 40.0 |
| Antibacterial agent | q.s. |
| Copolymer of tetrafluoroethylene & hexafluoropropylene | 1 |
| Perfume | q.s. |
| Water, purified     to | 100.0 |

Procedure: Add the triethanolamine lauryl sulfate solution. Disperse the copolymer. Stir in the remaining ingredients and continue to stir until uniform. In all preparations containing the perfluorocarbon or chlorotrifluoroethylene resins, the percentages may vary from 0.1–50%.

In the above actual copolymer formula, $n$ is an integer corresponding to the number of repeating units in the copolymerized chain.

The invention claimed is:

1. A hair and scalp conditioning and cleansing composition comprising about 1–50% by weight of a lubricating and scouring agent selected from the group consisting of chlorotrifluoroethylene polymer, the homopolymer of hexafluoropropylene, and the copolymer of tetrafluoroethylene and hexafluoropropylene having the formula $(CF_2CF_2-CF_2CFCF_3)_n$ wherein $n$ is an integer corresponding to the number of repeating units in the copolymerized chain, said polymers and copolymers each having a molecular weight of between about 1,000,000 and about 10,000,000, and the remainder of agents in the composition being selected from the group consisting of fatty alcohols, carboxypolymethylene, triethanolamine lauryl sulfate, methyl cellulose, lanolin, petrolatum, mineral oils and vegetable oils, and an antibacterial agent.

* * * * *